United States Patent [19]

Baur et al.

[11] 4,138,591
[45] Feb. 6, 1979

[54] MANUFACTURE OF ALKYLPHENOLS

[75] Inventors: Karl G. Baur, Ludwigshafen; Hans Hellbach, Frankenthal; Rolf Platz, Mannheim; Kurt Taglieber, Ludwigshafen, all of Fed. Rep. of Germany

[73] Assignee: BASF Aktiengesellschaft, Ludwigshafen, Fed. Rep. of Germany

[21] Appl. No.: 843,512

[22] Filed: Oct. 19, 1977

[30] Foreign Application Priority Data

Nov. 6, 1976 [DE] Fed. Rep. of Germany ....... 2650889

[51] Int. Cl.$^2$ ..................... C07C 37/22; C07C 39/06
[52] U.S. Cl. .................................................. 568/756
[58] Field of Search ........... 260/624 A, 624 C, 627 R; 568/756, 757

[56] References Cited

U.S. PATENT DOCUMENTS

| | | | |
|---|---|---|---|
| 2,163,227 | 6/1939 | Hund et al. | 260/624 A |
| 2,600,621 | 6/1952 | Fragen et al. | 260/624 A |
| 3,341,607 | 9/1967 | Leston | 260/624 A |
| 3,422,157 | 1/1969 | Kaufman et al. | 260/624 A |
| 3,940,451 | 2/1976 | Monroy | 260/624 A |

*Primary Examiner*—James O. Thomas, Jr.
*Assistant Examiner*—Werren B. Lone
*Attorney, Agent, or Firm*—Keil, Thompson & Shurtleff

[57] ABSTRACT

Alkylphenols are manufactured by reacting phenols with olefins, stripping the reaction mixture by means of an inert gas, cooling the phenol-containing gas mixture and removing the unconverted phenol. The products are starting materials for the manufacture of dyes, pesticides, pharmaceuticals, emsulfiers, dispersing agents, stabilizers, antioxidants, plasticizers, corrosion inhibitors, disinfectants, seed dressings, stabilizers against ageing, crop protection agents and scents.

12 Claims, No Drawings

MANUFACTURE OF ALKYLPHENOLS

The present invention relates to a new process for the manufacture of alkylphenols by reacting phenols with olefins, stripping the reaction mixture by means of inert gases, cooling the phenol-containing gas mixture and removing the unconverted phenol.

Ullmanns Encyklopädie der technischen Chemie, volume 13, pages 445–446 discloses that phenol can be reacted with olefins to give alkylphenols; the catalysts used are, in general, strong acids such as sulfuric acid, phosphoric acid and polyphosphoric acid, Friedel-Crafts compounds, such as aluminum chloride, boron fluoride, iron-III chloride, tin-II chloride or phosphorus oxychloride, acid aluminum oxide, $SiO_2$—$Al_2O_3$, aluminum phenolate or acid cation exchange resins. Syntheses without catalysts, eg. the alkylation of phenol with isobutylene at from 315° to 330° C. under pressure, have also been disclosed. Mixtures of products alkylated to different degrees are obtained, in which the products which are p-substituted or o- and p-substituted predominate. As disclosed by Ullmann (loc.cit., page 445), the ratio of the o-alkylphenols to the p-alkylphenols depends on the reaction conditions, eg. on the alkylation temperature. The reaction is frequently reversible. Dialkylphenols can be reacted with unsubstituted phenol to give monoalkyl compounds. Side-reactions which occur are isomerization, disproportionation reactions and rearrangement reactions at the phenol nucleus, polymerization of the olefins and etherification of the phenol. Accordingly, in the case of the tertiary butylation of p-cresol it is recommended to provide cooling such that the heat of reaction is removed as quickly as possible.

The alkylation reaction is frequently carried out with an excess of phenol over olefin in order to avoid higher substitution of the phenol by the olefin and thus to avoid losses in yield. The working up of the reaction mixture from such alkylations presents difficulties: On the one hand, unconverted olefin must be removed from the reaction mixture. Since the industrially available olefins are not single compounds and always contain small amounts of saturated hydrocarbons, small amounts of olefin or other hydrocarbons which have been left unconverted in the reaction cannot be recycled together with unconverted phenol to the alkylation reaction, since the concomitant materials would otherwise progressively accumulate if the reaction was carried out continuously. On the other hand, as high a proportion of unconverted phenol as possible must be separated from the end product and, advantageously, recycled to the reaction. The alkylphenol produced must also be freed from higher-boiling impurities.

In the removal of unconverted phenol from the alkylphenol, the distillation must furthermore be carried out under reduced pressure in order to keep the temperature, to which the phenolfree alkylphenols in the bottom of the distillation column are exposed, as low as possible. At high temperatures, alkylphenols tend to decompose, giving impure and discolored products. On the other hand, the removal of the unconverted phenol is the more difficult and the more incomplete, the lower is the distillation temperature, even if the column used has a high fractionating efficiency. The conventional removal of the unconverted phenol by distillation on an industrial scale therefore requires expensive distillation equipment and/or gives phenol contaminated by alkylphenols and causes decomposition and discoloration of the alkylphenols obtained as the end products. The conventional processes are therefore unsatisfactory in respect of yield, cost of equipment, and economical and simple operation.

We have found that alkylphenols are obtained advantageously by reacting unsubstituting or substituted phenol with olefins and separating the alkylphenols from the unconverted phenol, if, after the reaction, an inert gas heated to from 80° to 250° C. is passed through the reaction mixture formed, which is heated at from 80° to 250° C., the amount of gas passed through being from 0.3 to 6 parts by volume per hour per part by weight of starting phenol, and the gas is then cooled to from −40° to +100° C. and the phenolcontaining mixture which separates out on cooling the gas is isolated.

Further, we have found that the process is advantageously carried out by first cooling the gas, which has been passed through the reaction mixture, to from 11° to 100° C., removing the phenolcontaining mixture which has separated out, then adding to the gas, at the same temperature, an organic solvent vapor, thereafter cooling the gas/vapor mixture to from −40° to +11° C., and removing the phenol-containing mixture which has separated out.

In the present specification, parts by volume bear the same relation to parts by weight as that of the cubic meter to the kilogram.

If isobutylene is used, the reaction can be represented by the equation:

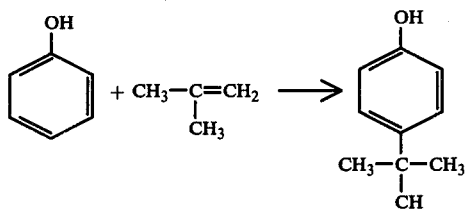

Compared to the conventional processes, the process of the invention surprisingly gives a large number of p-alkylphenols more simply and more economically, and in better yield and higher purity, particularly on an industrial scale and in continuous operation. The process is based on the observation that the formation of byproducts and decomposition products in the reaction mixture, and the discoloration of the alkylphenols, is less, and the yield of end product and of reusable unconverted starting phenol is greater, if inert gases are passed through the reaction mixture. The gases extract concomitant materials and/or impurities from the reaction mixture, and these can be isolated by condensation and fractional distillation. Accordingly, the gases act as auxiliaries for purifying the reaction mixture. In accordance with a definition given in "Introduction to Chemical Engineering" by W. L. Badger and J. T. Banchero (McGraw-Hill Book Comp. Inc. 1955), page 437 (last paragraph), the procedure described here is referred to as stripping. It is to be regarded as an advantage of the process of the invention that the inert gas not only strips the unconverted phenol from the reaction mixture, but also strips the residual olefins left unconverted during the alkylation reaction, as well as other lowboiling concomitant materials, eg. saturated hydrocarbons. By using the amount of inert gas prescribed according to the invention, and using the temperature to which, according to the invention, the inert gas is cooled after stripping the reaction mixture, the greater part of the pure phenol is isolated by condensation and the greater part of the olefins or other hydrocarbons remains in the inert gas. On recycling the phenol, no accumulation of olefins and/or hydrocarbons in the alkylation mixture occurs. Accordingly, a separate removal of residual olefin from the reaction mixture is unnecessary. The separation is sharper than those achieved by the processes of the prior art, and the proportion of end product in the phenol separated off, and in the off-gas, in less. Discoloration of the alkylphenols and the formation of decomposition products are only observed to a comparatively lesser degree, if at all. All these advantageous results are surprising in view of the prior art, since the relatively high temperature of the inert gas and of the reaction mixture during the passage of the inert gas (ie. during stripping) would have led to the expectation of increased decomposition and discoloration of the mixture, and the expectation of sidereactions between the unconverted starting materials, the end products and the decomposition products, eg. the formation of phenol-ethers, alkyl migration of the phenol nucleus, and disproportionation reactions. Furthermore, it is known that the alkyl groups of alkylaryl compounds can be split off again and/or undergo rearrangement, especially in the presence of acid compounds (Krauch-Kunz, Reaktionen der organischen Chemie (Hüthig Verlag, 1976, Heidelberg), pages 103–105; Organicum (14th edition, VEB Deutscher Verlag der Wissenschaften), pages 346–348, Olah, Friedel-Crafts and Related Reactions (Interscience, N.Y., 1963) volume I, pages 36 and 37, and March, Advanced Organic Chemistry, Reactions, Mechanism and Structure, page 433 (McGraw-Hill, N.Y., 1968)).

The reaction of the phenols with olefins can be carried out in the conventional manner, eg. in accordance with the above processes, described in Ullmann (loc.-cit., pages 444–446). Equally it is possible to carry out the alkylation of phenol with alkenes continuously, eg. by the method described in German Published Application DAS No. 1,443,346 or U.S. Pat. No. 2,802,884, using only coarse sulfonic acid resin exchangers of size 10–20 mesh; the catalyst forms a fixed bed in the reactor. Phenol can also be reacted continuously with olefins in the presence of an organic cation exchanger with sulfonic acid groups, which exchanger has a particle size of from 10 to 200 micrometers and is suspended in the liquid reaction mixture, the reaction being carried out, for example, in accordance with the method described in German Patent Application P 25 26 644.8.

Advantageous phenols to use are those of the formula

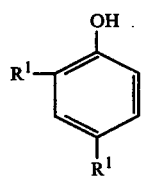   I.

and advantageous olefins are those of the formula

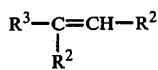   II, and accordingly advantageous alkylphenols in the reaction mixture are those of the formula

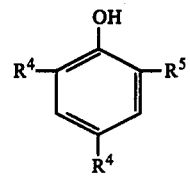   III, in which formulae the individual radicals $R^1$, $R^2$ and $R^3$ may be identical or different and each is an aliphatic radical, preferably alkyl of 1 to 9, especially of 1 to 4 carbon atoms, the individual radicals $R^1$ and $R^2$ may also be hydrogen, $R^3$ may also be an aromatic radical, preferably phenyl, or an araliphatic radical, preferably aralkyl or alkylphenyl of 7 to 12 carbon atoms, the individual radicals $R^4$ and $R^5$ may each be

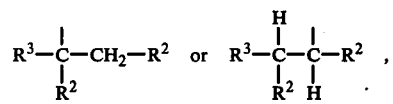

one radical $R^4$ and/or the radical $R^5$ may also be hydrogen, or each radical $R^4$ has the same meaning as $R^1$ if the radical $R^1$, present as a substituent on the same carbon atom, is an aliphatic radical. The above radicals may in addition be substituted by groups which are inert under the reaction conditions, eg. alkyl of 1 to 3 carbon atoms. The olefin preferably causes monosubstitution of the unsubstituted phenol in the p- or o-position, to a lesser degree produces disubstitution in the o- and p-positions or in the o- and o'-positions, and in general causes an ever lesser degree of trisubstitution in the o-, o'- and p-positions; accordingly, in the case of previously substituted phenols the olefin reacts at the p- or o-position which remains capable of substitution. The starting olefin may be reacted with a stochiometric amount or an excess of the phenol, preferably using a ratio of from 0.2 to 0.9, especially from 0.5 to 0.75 mole of starting material II per mole of phenol I. If a greater excess of starting material II, especially 2 or more moles, and advantageously from 2 to 3.5 moles, of starting material II is used per mole of phenol I, increasing amounts of o,p-dialkylphenols and/or o,o',p-trialkylphenols form, in accordance with the amount of starting material II. The use of branched alkenes is preferred. Mixtures of alkenes, eg. trimeric propylene or tetrameric propylene, and mixtures of alkenes and alkanes (ie. with concomitant hydrocarbon) such as are formed, for example, on cracking or dehydrogenating hydrocarbons, eg. petroleum, or oligomerizing olefins, especially isobutylene, propylene or n-butene, or hydrogenating carbon monoxide, may also be used. For the purpose of the present invention, trimeric propylene means a mixture, obtained on trimerizing propylene, of all unbranched or branched nonenes with the double bond in various positions.

By way of example, the following olefins may be used as starting materials II: n-pent-1-ene, n-hex-1-ene, n-hept-1-ene, n-oct-1-ene, n-non-1-ene; n-dec-1-ene, n-undec-1-ene, n-dodec-1-ene, prop-1-ene and n-but-1-ene; the above alkenes substituted in the 2-, 3- or 4-position by methyl, ethyl, n-propyl, isopropyl, n-butyl, isobutyl, sec.-butyl or tert.-butyl; 2,3-dimethyl-n-butene, 3,3-dimethyl-n-butene, 2,5-dimethylheptene, 3,3-dimethylheptene, 2,3,4-trimethylheptene, 2,4-dimethylheptene, 2,3-dimethylheptene, 4,4-dimethylheptene, 2,3-diethylhexene, 4,4-dimethylhexene, 2,3-dimethylhexene, 2,4-dimethylhexene, 2,5-dimethylhexene, 3,3-dimethylhexene, 3,4-dimethylhexene, 2-methyl-3-ethylpentene, 3-methyl-3-ethylpentene, 2,3,3-trimethylheptene, 2,4,4-trimethylpentene, 2,3,3-trimethylpentene, 2,3,4-trimethylpentene and 2,3,3,4-tetramethylpentene; corresponding alkenes where the double bond is in the 2-position or 3-position of the molecule; branched alkenes, such as are obtained as mixtures on dimerizing isobutene or n-butene (octenes) or trimerizing isobutene or n-butene (dodecenes) or propene (nonenes) or tetramerizing propene (dodecenes); styrene, o-methylstyrene, m-methylstyrene, p-methylstyrene, 3,4-dimethylstyrene, 2,4-dimethylstyrene, 2,5-dimethylstyrene, 2,6-dimethylstyrene, o-ethylstyrene, m-ethylstyrene, p-ethylstyrene, 3,4-diethylstyrene, 2,4-diethylstyrene, 2,5-diethylstyrene, 2,6-diethylstyrene, o-propylstyrene, m-propylstyrene, p-propylstyrene, o-isopropylstyrene, m-isopropylstyrene, p-isopropylstyrene, o-butylstyrene, m-butylstyrene, p-butylstyrene, o-isobutylstyrene, m-isobutylstyrene, p-isobutylstyrene, sec.-butylstyrene, m-sec.-butylstyrene, p-sec.-butylstyrene, o-tert.-butylstyrene, n-tert.-butylstyrene and p-tert.-butylstyrene.

The following are preferred: isobutene, diisobutene, triisobutene, styrene, α-methylstyrene, nonenes and dodecenes obtained by trimerizing and tetramerizing propene, 2,3-dimethyl-but-1-ene, 2-methyl-but-1-ene, 2-methyl-but-2-ene, 2-methyl-pent-1-ene, 2-methyl-hex-1-ene, 2-methyl-hept-1-ene, 2,3-dimethyl-pent-1-ene, 2,3-dimethyl-hex-1-ene and 2,4,4-trimethylpent-1-ene.

Suitable phenols I include phenol, o-methylphenol, o-ethylphenol, o-propylphenol, o-isopropylphenol, o-butylphenol, o-sec.-butylphenol, o-isobutylphenol, o-pentylphenol, o-hexylphenol, o-heptylphenol, o-octylphenol, o-nonylphenol, p-methylphenol, p-ethylphenol, p-propylphenol, p-isopropylphenol, p-butylphenol, p-isobutylphenol, p-sec.-butylphenol, p-pentylphenol, p-hexylphenol, p-heptylphenol, p-octylphenol, p-nonylphenol, o,p-dimethylphenol, o,p-diethylphenol, o,p-dipropylphenol, o,p-diisopropylphenol, o,p-dibutylphenol, o,p-diisobutylphenol, o,p-di-sec.-butylphenol, o,p-dipentylphenol, o,p-dihexylphenol, o,p-diheptylphenol, o,p-dioctylphenol, o,p-dinonylphenol, and phenols substituted by the above groups in the o- and p-position, but with the substituents being different, eg. o-methyl-p-ethyl-phenol.

Advantageous reaction mixtures contain alkylphenols III which are formed by alkylating the above individual compounds I by the above individual compounds II and which carry the alkyl substitutents in the o-, p-, o- and p-, o- and o'- and/or o-, o'- and p-position. For example, starting from unsubstituted phenol, suitable reaction mixtures are those which simultaneously contain o-alkylphenol, p-alkylphenol, o,p-dialkylphenol, o,o-dialkylphenol and o,o'-p-trialkylphenol.

The reaction is in general carried out at from 50° to 200° C., preferably from 70° to 130° C., under reduced pressure, superatmospheric pressure or atmospheric pressure, batchwise or, preferably, continuously. The residence time is preferably from 0.5 to 20, especially from 1 to 10, hours, and the throughput in continuous operation is preferably from 1 to 120, especially from 5 to 50, kilograms of starting material II per kilogram of catalyst per hour.

All the above catalysts, but preferably cation exchangers, may be used as the catalyst. In particular, organic cation exchangers containing sulfonic acid groups may be used; these are advantageously resins comprising sulfonated styrene-divinylbenzene copolymers, other sulfonated crosslinked styrene polymers, and phenol-formaldehyde or benzene-formaldehyde resins, containing sulfonic acid groups, the first-mentioned category being preferred. The exchangers are used in the acid form and not as the salt. The catalyst particle size is advantageously from 10 to 200, preferably from 20 to 180 and especially from 25 to 150 micrometers. Advantageously, the catalyst has a gel-like structure. Examples of suitable catalysts are the exchanger resins, commercially available under the trade mark ®LEWASORB A-10. Equally, other resins commercially available under trade marks eg. ®Amberlit IR-120, ®Dowex 50, ®Lewatit S-100, ®Nalcite HCR, ®Permutit RS and ®Wofatit KPS-200 may be milled to the particle size according to the invention, and used in this form. Advantageously, the resins are dehydrated in the conventional manner before use, eg. by heating at 100° C. under reduced pressure. They can however also be dehydrated by displacing the water by means of hydrophilic organic liquids and then heating the material at 100° C. under reduced pressure, or by azeotropic distillation with an organic liquid.

In a preferred embodiment of the process, the catalyst is in suspension — as a rule in the reaction mixture undergoing formation — during the reaction. Advantageously, a part of the liquid phenol I or of the starting mixture of phenol I and olefin II is introduced into the reaction vessel and the catalyst is suspended therein with thorough mixing. Advantageously, no additional solvent is used. In the case of mixtures of starting materials II, eg. obtained from cracking petroleum, the saturated hydrocarbons contained in the mixture may be used as the liquid medium for the suspension. The amount of initially introduced phenol or starting mixture and/or organic solvent is so chosen that the catalyst is suspended in the reaction mixture undergoing formation, in an amount of from 0.3 to 10, preferably from 1 to 3, percent by weight of catalyst based on the weight of the total liquid mixture in the reaction space. Advantageously, the reaction mixture is mixed thoroughly throughout the reaction, preferably by stirring at not less than 300, advantageously from 400 to 2,000, and especially from 500 to 1,000, revolutions per minute. If mixing devices without stirrers are used, those which apply to the mixture a shearing energy corresponding to the above rates of stirring are preferred. Mixing may also be effected by means of an inert gas, eg. nitrogen. This gives a fine suspension. Provided the above mixing conditions are observed, a broad range of conventional stirring devices may be used, namely injectors, ball jets, vortex jets, turbine stirrers, mixing nozzles, Lechler mixing nozzles, paddle stirrers, anchor stirrers, bar-type stirrers, propeller stirrers, Cramer stirrers, vibro-mixers, finger-type stirrers, crossbeam stirrers, gyratory stirrers, grid stirrers, flat stirrers, spiral turbines, scoop stirrers, planetary stirrers, centrifugal gyratory stirrers, rotating atomizers, ejectors, triangular stirrers, hollow stirrers, tubular stirrers and impeller stirrers. It is also possible to use equipment and installations such as stirred kettles, stirred kettle cascades, flow tubes, airlift type stirring units, homogenizing equipment, gyratory mixers, turbo-mixers, emulsifying centrifuges, ultrasonic tubes, flow mixers, rotating drums, chamber reactors, circulatory reactors, loop reactors, cellular reactors, screw reactors, bubble columns, jet scrubbers, liquid ring pumps, ejector-type tubular reactors and thin film reactors; for economic reasons, stirred kettles are preferred.

The reaction may advantageously be carried out as follows: A liquid mixture of starting material II and phenol I is passed through the suspension of the catalyst in the starting mixture or reaction mixture at the reaction temperature and reaction pressure, and is then filtered. Filtration is advantageously effected before the suspension leaves the reactor. Suitable filters are acidresistant filter cloths, wire mesh filters and sinter metal filters, provided the mesh sizes and pore diameters are smaller than the catalyst particles. Continuous centrifuges may also be used with advantage to separate off the catalyst.

After the reaction, it is advantageous to filter off all the above solid catalysts in the manner described. Gaseous catalysts, eg. boron trifluoride, are also advantageously removed before starting the process according to the invention, eg. by heating the reaction mixture at from 150° to 200° C. Liquid catalysts, or catalysts dissolved in the reaction mixture, may remain in the mixture but if substantial amounts of acid are present the greater part of the acid may be neutralized with bases, eg. with alkali metal hydroxides, eg. sodium hydroxide, or, preferably, with aliphatic amines, eg. alkylamines of 8 to 12 carbon atoms, eg. octylamine or dibutylamine, or alkanolamines of 2 to 4 carbon atoms, having the hydroxy group in the ω-position, eg. ethanolamine or diethanolamine, or aromatic amines, eg. aniline.

Reaction mixtures advantageously usable for the process of the invention contain from 10 to 70, preferably from 20 to 50, percent by weight of the unconverted phenol I, from 1 to 50, preferably from 1 to 10, percent by weight of the unconverted olefin II, from 20 to 80, preferably from 50 to 70, percent by weight of alkylphenol III, and from 0.1 to 20, preferably from 0.5 to 5, percent by weight of concomitant hydrocarbons. The reaction mixture is next heated to from 80° to 250° C., preferably from 150° to 200° C., and is kept at this temperature whilst passing an inert gas through it.

The inert gas may contain one or more inert gaseous materials. The amount of inert gas used is from 0.3 to 6 parts by volume, preferably from 0.7 to 3 parts by volume, per part by weight of starting phenol, preferably per part by weight of phenol I, per hour of throughput of the inert gas. Starting phenol or phenol I means the total amount of phenol used which is present in the reaction mixture after the reaction, essentially as end product III and unconverted phenol I. Suitable solvents for generating inert vapors are those which boil below 175° C., preferably below 150° C. and especially at from 30° to 135° C. Examples of suitable inert gases are rare gases, eg. xenon, argon, neon and helium; alkanes, eg. methane, ethane, propane, 2,2-dimethylpropane, butane, pentane and isobutane; gaseous halohydrocarbons, eg. tetrafluoromethane, dichloromethane, chloromethane, bromomethane, hexafluoroethane, chloroethane and fluoroethane; gaseous organic compounds of inorganic elements, eg. tetramethylsilane; ethers, eg. dimethyl ether and methyl ethyl ether, and, preferably, nitrogen, hydrogen, carbon monoxide and/or carbon dioxide and corresponding mixtures, preferably mixtures of carbon monoxide, carbon dioxide and hydrogen, as frequently obtained as residual gases from cracking units. The vapors of the following organic solvents may, for example, be used, provided the boiling point is below 175° C.: aromatic hydrocarbons, eg. benzene, ethylbenzene, toluene and xylenes, aliphatic and cycloaliphatic hydrocarbons, eg. petroleum ether, hexane, methylcyclohexane, octane, cyclopentane and cyclohexane, cyclic ethers, eg. dioxane and tetrahydrofuran, chlorohydrocarbons, eg. chloroform, carbon tetrachloride, methylene chloride, 1,2-dichloroethane and chlorobenzene, aliphatic ethers, eg. 1,1-dimethoxyethane, ethyl propyl ether and diisopropyl ether, or mixtures of these. Steam is less suitable in the case of the unsubstituted phenol I, since it results in the known difficulty of separating a phenol/water mixture into its pure components after it has been condensed. The inert gases are introduced at from 80° to 250° C., preferably from 150° to 220° C., and are in general passed continuously through the reaction mixture under a pressure of from 0.1 to 5, preferably from 1 to 1.5, bars. Advantageously, the inert gas is passed through the reaction mixture in a reactor with more than 4, preferably from 8 to 50, and especially from 10 to 20, stages, with each stage providing the portion of the inert gas which has not been charged in the preceding stage with a renewed opportunity of stripping the reaction mixture. Such a multistage reactor may be, for example, a cascade reactor, a plurality of stirred kettles connected in series or, preferably, tray columns, eg. perforated tray columns, eg. perforated tray columns, Oldershaw columns, glass tray columns, bubble-cap tray columns and valve tray columns, with the mixture and inert gas advantageously flowing in counter-current through the reactor. Advantageously, tray columns which permit a flow velocity of the inert gas of from 0.1 to 1 meter per second are used. In the bubble-cap tray columns the ratio of weir height to diameter is from 0.2 to 0.4, whilst in the case of ballvalve tray columns and perforated tray columns perforation diameters of from 5 to 15 mm, ball diameters of from 8 to 30 mm and tray spacings of from 300 to 800 mm are preferred. Packed columns filled with Raschig rings, Pall rings or saddle packings are also suitable.

During stripping of the reaction mixture, the inert gases in general take up from 50 to 100, preferably from 98 to 100, percent by weight of the total unconverted phenol I, from 90 to 100, preferably from 98 to 100, percent by weight of the total unconverted olefin II, from 0.1 to 20, preferably from 1 to 5, percent by weight of the total alkylphenol III, and from 90 to 100, preferably from 98 to 100, percent by weight of the total concomitant hydrocarbons. Advantageously, the gas stream after stripping carries, per part by volume of inert gas, from 0.3 to 3, preferably from 0.7 to 1.4, parts by weight of phenol I, from 0.03 to 0.3, preferably from 0.07 to 0.14, part by weight of olefin II, from 0.01 to 1, preferably from 0.05 to 0.1, part by weight of alkylphenol III and from 0.01 to 1, preferably from 0.01 to 0.05, part by weight of concomitant hydrocarbons. The inert gas (stripping gas) laden with the above materials is then cooled in one step to from $-40°$ C. to $+100°$ C., preferably to from $+35°$ to $+50°$ C., but may also be cooled in several steps, preferably in 2 steps. For example, the stripping gas is cooled in 2 steps, first to from $+11°$ C. to $+100°$ C., preferably to from 35° to 50° C., and then to from $-40°$ to $+11°$ C., preferably to from $-30°$ to 0° C. The cooling steps are carried out continuously and under atmospheric or superatmospheric pressure, preferably at the pressure selected for the stripping process. Of the total material with which the stripping gas is laden, the following amounts are separated out by condensation and are, as a rule, collected, in the case of indirect cooling, in a vessel downstream from the condenser and, in the case of direct cooling effected by circulating the condensate, are collected in the said condensate:

1-Stage cooling: from 70 to 99 percent by weight of the phenol I contained in the stripping gas, from 10 to 70 percent by weight of the olefin II contained in the stripping gas, from 80 to 99.9 percent by weight of the alkylphenol III contained in the stripping gas and from 10 to 70 percent by weight of the concomitant hydrocarbons contained in the stripping gas.

In the case of 2-stage cooling, in the 1st stage: from 70 to 99 percent by weight of the phenol I contained in the stripping gas, from 10 to 70 percent by weight of the olefin II contained in the stripping gas, from 80 to 99.9 percent by weight of the alkylphenol III contained in the stripping gas, and from 10 to 70 percent by weight of the concomitant hydrocarbons contained in the stripping gas.

In the case of 2-stage cooling, in the 2nd stage: from 90 to 100 percent by weight of the phenol I remaining in the stripping gas after cooling in the 1st stage, from 80 to 100 percent by weight of the olefin II remaining in the stripping gas after cooling in the 1st stage, from 95 to 100 percent by weight of the alkylphenol III remaining in the stripping gas after cooling in the 1st stage and from 80 to 100 percent by weight of the concomitant hydrocarbons remaining in the stripping gas after cooling in the 1st stage.

The separation can be improved by adding an auxiliary to the inert gas or stripping gas, in general after stripping and shortly before cooling, advantageously before starting the 2nd cooling stage in the case of 2-stage cooling. Suitable auxiliaries are organic solvents which are in the form of their vapor at the particular cooling temperature, advantageously ketones, eg. methyl ethyl ketone, acetone, diisopropyl ketone, diethyl ketone, methyl isobutyl ketone, mesityl oxide, acetophenone, cyclohexanone, ethyl isoamyl ketone, diisobutyl ketone, methylcyclohexanone and dimethylcyclohexanone, alkanols and cycloalkanols, eg. ethanol, methanol, n-butanol, isobutanol, tert.-butanol, glycol, glycerol, n-propanol, isopropanol, amyl alcohol, cyclohexanol, 2-methyl-4-pentanol, ethylene glycol monoethyl ether, 2-ethylhexanol, methylglycol, n-hexanol, isohexyl alcohol, isoheptyl alcohol, n-heptanol, ethylbutanol, nonyl alcohol, dodecyl alcohol, methylcyclohexanol and diacetone-alcohol, especially those of 1 to 5 carbon atoms, ethylene glycol, 1,2-propylene glycol, 1,3-propylene glycol, 1,2-butanediol, 1,4-butanediol, 2,3-butanediol, 1,3-butanediol, diethylene glycol, triethylene glycol and tetraethylene glycol which are unsubstituted or are mono-etherified by methyl, ethyl, n-propyl, isopropyl, n-butyl, isobutyl, sec.-butyl, or tert.-butyl, or are dietherified by two such groups, which may be identical or different, corresponding polyglycols containing from 2 to 10 molecules of 1,2-propylene glycol, with or without ethylene glycol, as chain members, and their correspondingly substituted monoethers and diethers, and appropriate mixtures. Advantageously the amount of solvent used is from 10 to 500 percent by weight, preferably from 50 to 200 percent by weight, based on the phenol I in the stripping gas or, in the case of 2-stage cooling, remaining in the stripping gas after the 1st cooling stage. Advantageously, the solvent is led in countercurrent to the stripping gas, the process being advantageously carried out in one of the above reactors, preferably in one of the above columns. In a preferred embodiment, in the case of 2-stage cooling, the 2nd cooling step and the addition of the auxiliary in counter-current to the stripping gas are carried out simultaneously in such a column. In continuous operation a proportion of the circulating material which corresponds to the amount of added auxiliary and to the amount of condensate formed is withdrawn continuously; phenol, and the auxiliary, can be recovered from the withdrawn material by rectification. In a particularly advantageous embodiment of the second cooling stage, direct cooling is effected by pumping the mixture of condensate and auxiliary through a column in countercurrent to the inert gas. In this case, the auxiliary is fed as a liquid into the mixture which is circulated by pumping. After cooling, advantageously carried out in two stages, the stripping gas can be recycled; similarly, the unconverted phenol obtained in the 1st cooling stage can, without further working up, by recycled to the reaction with olefin.

The p-alkylphenols I which may be manufactured by the process of the invention are valuable starting materials for the manufacture of dyes, pesticides, pharmaceuticals, emulsifiers, dispersing agents, stabilizers, antioxidants, plasticizers, corrosion inhibitors, disinfectants, seed dressings, anti-aging stabilizers, crop protection agents and scents. Regarding their use, reference may be made to the above publications, Ullmanns Encyklopädie der technischen Chemie, volume 13, pages 440–447, and Kirk-Othmer, Encyclopedia of Chemical Technology, volume I, pages 901–916 (2nd edition).

In the Examples which follow, parts are by weight.

EXAMPLE 1

(a) Reaction

A suspension of 1,000 parts of phenol and 50 parts of exchanger resin is prepared in a stirred reactor by stirring at a speed of 500 revolutions per minute (specific stirring energy 0.4 kilowatt/m$^3$ of reactor contents) at 110° C. and 1 bar and 660 parts of trimeric propylene (70 percent by weight of n-nonenes and 30 percent by weight of iso-nonenes) are passed in. The exchanger resin is a sulfonated styrene-divinylbenzene copolymer resin which has been dehydrated, before use, for 20 hours at 100° C. under reduced pressure; it has a gel structure and a particle size of from 20 to 150 micrometers. The suspension in the reactor is then stirred continuously at 500 revolutions per minute, and after 6 hours, 1,000 parts of phenol and 660 parts of trimeric propylene are passed in per hour. After a residence time of 8 hours, 500 parts of phenol, 6.6 parts of trimeric propylene and concomitant hydrocarbons, and 1,153.4 parts of nonylphenol are withdrawn continuously per hour. The mixture withdrawn is filtered through a suction line fitted with a metal filter (pore diameter 10 micrometers) and is fed to a distillation column.

(b) Treatment of the reaction mixture

The reaction mixture contains 30.1 percent by weight of phenol, 0.3 percent by weight of trimeric propylene, 59.4 percent by weight of p-nonylphenol, 6.6 percent by weight of o-nonylphenol, 3.2 percent of weight of o,p-dinonylphenol, 0.2 percent by weight of o,o'-dinonylphenol, 0.1 percent by weight of o,o',p-trinonylphenol and 0.1 percent by weight of concomitant hydrocarbons (saturated hydrocarbons of 9 carbon atoms). It is heated to 185° C. and fed to the top of a column. In this column, a gaseous mixture of 579 parts of nitrogen and 2.24 parts of a residual charge comprising 3.5 percent by weight of phenol, 57.8 percent by weight of trimeric propylene, 6.4 percent by weight of concomitant hydrocarbons (saturated hydrocarbons of 9 carbon atoms) and 32.3 percent by weight of isopropanol is led, per hour, upward in counter-current to 1,660 parts of reaction mixture. The column has 32 actual trays. On the 20th tray (from the bottom) the liquid rising from above is heated and kept at 180° C. The inert gas fed in is at 200° C. At the bottom of the column, 1,116.4 parts of nonylphenol of boiling point 301° C. (96.8 percent of the total nonylphenol introduced at the top of the column), and the above dinonylphenols and trinonylphenol, are withdrawn per hour. The average pressure in the column is 1 bar. The inert gas is fed in at the bottom of the column. The stripping gas (1,119 parts per hour) leaving the column at the top is composed of 44.17 percent by weight of phenol, 0.73 percent by weight of trimeric propylene and concomitant hydrocarbons, 3.31 percent by weight of o- and p-nonylphenol, 51.72 percent by weight of nitrogen and 0.07 percent by weight of isopropanol. It is cooled to 41° C. in a heat exchanger. 527.6 parts of condensate composed of 93 percent by weight of phenol and 7 percent by weight of o- and p-nonylphenol separate out per hour and are recycled to a fresh alkylation. The stripping gas is then introduced at the bottom of a 2nd column having 5 trays. In this column, 2.38 parts per hour of fresh isopropanol at −20° C. are fed in at the top and led in counter-current to the stripping gas. The material from the bottom of the 2nd column is recycled to the top of the 2nd column. The fresh isopropanol is introduced at the top into this circulating material. From the bottom of the column, 12.98 parts per hour of a condensate composed of 29.5 percent by weight of phenol, 47.1 percent by weight of trimeric propylene, 5.2 percent by weight of concomitant hydrocarbon and 18.2 percent by weight of isopropanol are withdrawn. This material is subjected to fractional distillation and the unconverted phenol is recycled to the reaction. The stripping gas which leaves the top of the column at −20° C. is heated to 200° C. in a heat exchanger and then fed to the 1st column (stripping column). In total the material obtained per hour, after distillation at 10 mm Hg, is 1,059.5 parts of colorless o- and p-nonylphenol (95% of theory) of boiling point 153° C./10 mm Hg, and 56.9 parts of the above dinonylphenols and trinonylphenols. In total, 494.5 parts of unconverted phenol are recycled to the reaction.

EXAMPLE 2 (COMPARATIVE EXPERIMENT)

If the reaction is carried out as described in Example 1a, but after filtration the reaction mixture obtained is passed to a fractional distillation instead of to the treatment with inert gas, a bottom temperature of 195° C. is required in an 8-tray column, and 1,000 parts per hour of a yellowish nonylphenol of boiling point 153°–158° C./10 mm Hg are obtained. The unconverted phenol can no longer be recycled to the continuous reaction, since the concomitant hydrocarbons referred to in 1b) contaminate the phenol.

We claim:

1. In a process for the manufacture of alkylphenols of the formula

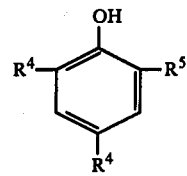

in which an unsubstituted or substituted phenol of the formula

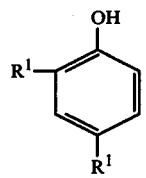

is reacted with an olefin of the formula

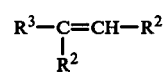

to form a reaction mixture containing alkylphenols and unreacted phenol in which the individual radicals $R^1$, $R^2$ and $R^3$ may be identical or different and each is an alkyl of 1 to 9 carbon atoms, the individual radicals $R^1$ and $R^2$ may also be hydrogen, $R^3$ may also be phenyl, or an aralkyl or alkylphenyl of 7 to 12 carbon atoms, the individual radicals $R^4$ and $R^5$ may each be

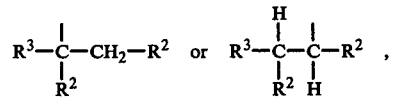

one radical $R^4$ and/or the radical $R^5$ may also each be hydrogen, or each radical $R^4$ has the same meaning as $R^1$ if the radical $R^1$, present as a substituent on the same carbon atom, is an aliphatic radical, wherein the above radicals may in addition be substituted by alkyl of 1 to 3 carbon atoms, and in which the formed alkylphenols are separated from the unconverted phenol, the improvement which comprises:

passing an inert gas heated to from 80° to 250° C. through the reaction mixture, which reaction mixture is heated to from 80° to 250° C., the amount of gas passed through the mixture being from 0.3 to 6 parts by volume per hour per part by weight of starting phenol; cooling the thus laden gas to from −40° to +100° C.; and isolating the phenol-containing mixture which separates out on cooling the gas.

2. A process as set forth in claim 1, in which the gas passed through the reaction mixture is first cooled to from 11° C. to 100° C., the phenol-containing mixture which separates out is separated off, at least one organic solvent auxiliary in the form of its vapor is added to the gas at this temperature, the gas/vapor mixture is then cooled to from −40° C. and +11° C., and the phenol-containing mixture which has separated out is isolated.

3. A process as set forth in claim 1 in which the reaction is carried out at from 50° to 200° C. with an organic cation exchanger which contains sulfonic acid groups and is in suspension in the reaction medium undergoing formation.

4. A process as set forth in claim 1 in which a reaction mixture which contains from 10 to 70 percent by weight of the total unconverted phenol I, from 1 to 50 percent by weight of the total unconverted olefin II, from 20 to 80 percent by weight of alkylphenol III and from 0.1 to 20 percent by weight of concomitant hydrocarbons is used.

5. A process as set forth in claim 1 in which the reaction mixture is heated from 150° to 200° C. and is kept at this temperature whilst passing the inert gas through it.

6. A process as set forth in claim 1 in which from 0.7 to 3 parts by volume of inert gases are used per part by weight of starting phenol per hour of throughput of the inert gas.

7. A process as set forth in claim 1 in which an inert gas at from 150° to 220° C. is used.

8. A process as set forth in claim 1 in which, after the reaction, the reaction mixture is filtered if necessary and the inert gas is passed through the reaction mixture at a pressure of from 0.1 to 5 bars in a reactor comprising more than 4 stages, in each stage of which the proportion of the inert gas not laden in the preceding stage has a renewed opportunity for stripping.

9. A process as set forth in claim 1 in which each part by volume of inert gas in the gas stream after stripping is laden with from 0.3 to 3 parts by weight of phenol I, from 0.03 to 0.3 part by weight of olefin II, from 0.01 to 1 part by weight of alkylphenol III and from 0.01 to 1 part by weight of concomitant hydrocarbons.

10. A process as claimed in claim 1, in which the auxiliary used is a ketone, an alkanol, a cycloalkanol, or ethylene glycol, 1,2-propylene glycol, 1,3-propylene glycol, 1,2-butanediol, 1,4-butanediol, 2,3-butanediol, 1,3-butanediol, diethylene glycol, triethylene glycol, tetraethylene glycol and/or a polyglycol, each of which diols may be unsubstituted or mono-etherified by methyl, ethyl, n-propyl, isopropyl, n-butyl, isobutyl, sec.-butyl or tert.-butyl, or dietherified by two identical or different groups, amongst the above.

11. A process as set forth in claim 1 wherein the laden inert gas is cooled in one step to from +35° to +50° C.

12. A process as set forth in claim 1 wherein the laden inert gas is cooled in two steps, first to from 35° to 50° C. and then to from −30° to 0° C.

* * * * *